US012788837B2

(12) United States Patent
Maier et al.

(10) Patent No.: US 12,788,837 B2
(45) Date of Patent: Nov. 10, 2026

(54) FLUID INTERCEPTION DEVICE FOR A MEDICAL CLEANING SYSTEM

(71) Applicant: W & H STERILIZATION S.r.l., Brusaporto (IT)

(72) Inventors: Klaus Maier, Brusaporto (IT); Marino Luigi Magno, Brusaporto (IT); Marco Barigazzi, Brusaporto (IT); Alex Crotti, Brusaporto (IT); Andrea Bianchi, Brusaporto (IT); Angelo Cornelli, Brusaporto (IT); Daniele Bettineschi, Brusaporto (IT)

(73) Assignee: W & H STERILIZATION S.R.L., Brusaporto (IT)

( * ) Notice: Subject to any disclaimer, the term of this patent is extended or adjusted under 35 U.S.C. 154(b) by 577 days.

(21) Appl. No.: 18/357,527

(22) Filed: Jul. 24, 2023

(65) Prior Publication Data

US 2024/0033388 A1 Feb. 1, 2024

(51) Int. Cl.
*A61L 2/26* (2006.01)
*A61L 2/18* (2026.01)
(Continued)

(52) U.S. Cl.
CPC .................. *A61L 2/26* (2013.01); *A61L 2/18* (2013.01); *B01D 5/0051* (2013.01);
(Continued)

(58) Field of Classification Search
CPC .......... A61L 2/26; A61L 2/18; A61L 2103/15; A61L 2202/122; A61L 2202/14;
(Continued)

(56) References Cited

U.S. PATENT DOCUMENTS 2,491,060 A * 12/1949 Robinson ........... B01D 11/0226 34/74
2,500,774 A * 3/1950 Sebald .................... C02F 5/025 210/97
(Continued)

FOREIGN PATENT DOCUMENTS

DE 102009013662 A1 10/2010
EP 3006619 B1 8/2018
(Continued)

OTHER PUBLICATIONS

Escapenet machine translation of WO2010106159A1, Sep. 23, 2010. (Year: 2010).*
(Continued)

*Primary Examiner* — Joseph W Drodge
(74) *Attorney, Agent, or Firm* — NIXON & VANDERHYE

(57) ABSTRACT

Disclosed is a fluid interception device for a cleaning and disinfecting system for medical devices, equipped with a processing chamber, including a hollow box-shaped condenser body, including: a transit port, in fluid communication with a transit duct of the cleaning and disinfecting system; and a vent port in communication with the external environment. The hollow box-shaped condenser body includes: condensation nozzles, in fluid communication with drain holes in a lower portion of the hollow box-shaped condenser body; and water feeding nozzles, above and in fluid communication with the transit port. Between the condensation nozzles and water feeding nozzles, a separation septum being arranged which defines and divides a condensation chamber and a feeding chamber. The transit port is arranged on the side of the feeding chamber and the separation septum providing at least one flow port which
(Continued)

places the transit port in communication with the condensation chamber.

9 Claims, 4 Drawing Sheets

(51) Int. Cl.
*B01D 5/00* (2006.01)
*A61L 103/15* (2026.01)

(52) U.S. Cl.
CPC ......... *B01D 5/0057* (2013.01); *B01D 5/0069* (2013.01); *A61L 2103/15* (2026.01)

(58) Field of Classification Search
CPC ............. A61L 2202/15; A61L 2202/17; A61L 2202/123; A61L 2/07; F28B 3/04; F28C 3/08; A61B 90/70; B01D 1/16; B01D 1/20; B01D 5/0027; B01D 5/0033; B01D 5/0051; B01D 5/0057; B01D 5/006; B01D 5/0069; A61C 19/002
IPC ......... F28B 3/04; F28C 3/08; B01D 1/16,1/20, 5/0027, 5/0033, 5/0051, 5/0057, 5/006, 5/0069
See application file for complete search history.

(56) References Cited

U.S. PATENT DOCUMENTS

| | | | | | |
|---|---|---|---|---|---|
| 2,684,231 | A * | 7/1954 | Pomykala | F28B 3/04 | 261/78.2 |
| 3,471,373 | A * | 10/1969 | Potthgarst, Jr. | B01D 1/2896 | 202/202 |
| 3,849,259 | A * | 11/1974 | Steinbruchel | C02F 1/06 | 159/DIG. 13 |
| 4,874,406 | A * | 10/1989 | Bekedam | B05B 1/265 | 96/174 |
| 4,938,933 | A * | 7/1990 | Perrot | A61B 90/70 | 134/100.1 |
| 4,988,485 | A * | 1/1991 | Bene | A61C 19/002 | 239/419 |
| 5,173,259 | A * | 12/1992 | Bordini | A61L 2/20 | 53/167 |
| 5,405,435 | A * | 4/1995 | Bekedam | B01D 19/0042 | 96/174 |
| 6,282,497 | B1 * | 8/2001 | Bharathan | F28B 3/02 | 702/30 |
| 2012/0298151 | A1 * | 11/2012 | Heckenberger | A61L 2/07 | 422/292 |
| 2017/0069199 | A1 * | 3/2017 | Magno | G08C 17/02 | |
| 2018/0052454 | A1 * | 2/2018 | Magno | A61C 19/002 | |
| 2022/0370665 | A1 * | 11/2022 | Dejarme | A61L 2/06 | |

FOREIGN PATENT DOCUMENTS

| | | | | |
|---|---|---|---|---|
| JP | 2001518175 A * | 10/2001 | | F28F 25/06 |
| WO | WO-2010106159 A1 * | 9/2010 | | A61C 19/002 |

OTHER PUBLICATIONS

English Machine translation of WO201006159A1, Sep. 23, 2010 (Year: 2010).*
Search Report for IT202200015843, dated Mar. 10, 2023, 7 pages.

* cited by examiner

FLUID INTERCEPTION DEVICE FOR A MEDICAL CLEANING SYSTEM

CROSS REFERENCE TO RELATED APPLICATIONS

This application claims priority to IT Patent Application No. 102022000015843 filed Jul. 27, 2022, the entire contents of which is hereby incorporated by reference.

BACKGROUND OF THE INVENTION

Field of the Invention

The present invention relates to a cleaning system for medical apparatus and, in particular, a device for intercepting cleaning fluids to be applied to such a cleaning system.

Description of the Related Art

As is known, medical apparatus, including surgical instruments, dental handpieces, dental turbines and so on (also, in the reference regulations, said medical devices), require careful cleaning after every use. In particular, before being sterilized and packed for preservation, such medical apparatus is cleaned in appropriate cleaning and disinfecting systems, such as thermo-disinfectors.

These systems provide for accommodating medical apparatus inside a cleaning chamber, which hereinafter will be referred to as “processing chamber”, inside which a cleaning, disinfecting and sometimes even a drying cycle are carried out, involving the introduction and expulsion of working fluids. In particular, the working cycle typically involves introducing water for cleaning, sometimes softened water and possibly even demineralized water, and exhausting steam for disinfection and possible drying.

The applicable regulations in the medical sector provide some constraints in the processing of working fluid, especially if the system is directly coupled to the water supply network for the supply of water. In particular, it is necessary to both provide a configuration which prevents a backflow or siphoning of fluids towards the water supply network from which the water is drawn (EN 61770), and devices which avoid the direct emission of exhaust steam into the environment (UNI EN ISO 15883-1).

These two requirements are addressed in various ways by manufacturers of cleaning and disinfecting systems, normally providing ad hoc devices for each working fluid. For example, on the one hand, in the water feeding circuit, vacuum break interception valves and/or air break or air gap units are provided, which ensure an air separation between a water feed duct and the water usage circuit, such that any backflow of contaminated water towards the water supply network cannot occur. On the other hand, in the steam outlet circuit, appropriate traps and condensers are provided, which are placed between the steam outlet port and the external environment.

For example, DE 102 009 013 662 discloses a steam condenser, comprising a hollow body in which a condensation path is provided in which condensation nozzles are inserted. EP 3 006 619 discloses a similar steam condenser. Both these devices are concerned only with the steam disposal circuit.

This design approach has some drawbacks. First of all, the two working fluid circuits are kept separate and therefore provide separate feeding/discharge ports in the processing chamber, as well as specific space requirements in the system. This results in design complexity and an increase in costs. Furthermore, in the event that these circuits fail or become obstructed, it is necessary to intervene on the entire system and proceed with precise diagnostics to identify and replace defective components, thereby bringing the entire system to an operational standstill.

The Applicant has set out with the objective to rationalize these working fluid interception devices, so as to address, at least partly, the existing drawbacks.

SUMMARY OF THE INVENTION

The object of the present invention is therefore to provide a working fluid interception device which overcomes the drawbacks of the prior art.

In particular, it is intended to provide a working fluid interception device in a cleaning, disinfecting and possible drying system, which is more compact, simple to maintain and minimizes the costs of interfacing with a processing chamber in which said working fluids are used.

These objects are achieved by means of a device as described in essential terms in the accompanying claims.

BRIEF DESCRIPTION OF THE DRAWINGS

Other features and advantages of the invention will become clearer from the following detailed description of an embodiment, given by way of example and in a non-limiting manner, and illustrated in the appended drawings in which.

DETAILED DESCRIPTION

The device here disclosed can be applied to any cleaning and disinfecting system into which cleaning water (possibly softened and/or demineralized) will need to be fed and from which steam will need to be extracted, with a possible drying phase. For the sake of convenience, hereinafter reference will be made to a cleaning and disinfecting system specifically intended for medical devices, but it will not be described further in detail since it is not per se the subject of the present invention.

Figure 1:
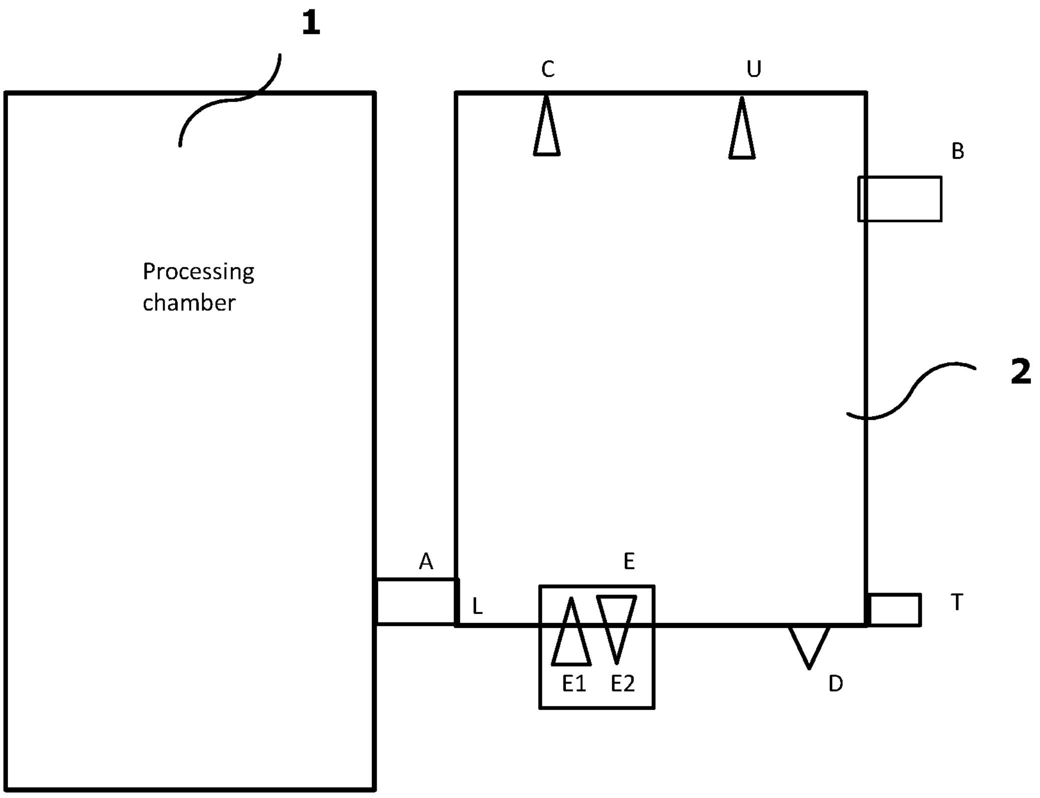
FIG. 1 is a conceptual diagram of the device according to the invention, in which the orientation of the various components is not real.

In FIG. 1, a cleaning or processing chamber 1 of the cleaning and disinfecting system has been represented schematically in a simple manner, connected to a fluid interception device 2 by means of at least one transit duct A for the working fluids inside and outside the processing chamber 1.

The interception device 2 (FIG. 1) is composed substantially of a hollow condenser body, provided with a transit port L, in communication with the transit duct A, and a vent port B which places the device in communication with the external environment. According to a peculiar feature of the invention, in the hollow condenser body, one or more condensation nozzles U are also incorporated, which are in fluid communication with one or more drain holes D, together with one or more water feeding nozzles C in communication with the same transit duct A and with possibly even a softened water supply duct equipped with a vacuum break unit E.

The condensation nozzles U have an area where sprayed water comes out, for purposes which will be illustrated better later on.

The hollow condenser body is fitted to the cleaning system such that the transit duct A is connected in a sealed manner to the transit port L, with such an attitude that defines an upper portion and a lower portion of the interception device 2. In other words, the interception device 2 is fitted with respect to the processing chamber 1 with a pre-established orientation, to correctly exploit the various components and obtain the desired progression of fluids.

To this end, drain hole or holes D are arranged in the lower portion, i.e. at a lower level relative to the water feeding nozzles C and also relative to the area where sprayed water leaves the condensation nozzles U. Similarly, the transit port L is arranged in the lower portion, at a lower level than the water feeding nozzles C.

This is consistent with the characteristics and operation of the working fluids which pass through the interception device: water is fed from the water feeding nozzles C placed in the upper portion and precipitates by gravity until it enters the processing chamber 1 by the transit port L; the disinfecting steam leaves the processing chamber 1 and, via the transit port L, rise from the lower portion inside the hollow condenser body and is cooled with the aid of the condensation nozzles U, while the condensate liquid which gradually precipitates downwards is disposed of via the drain holes D.

Preferably, a water presence detection sensor T is furthermore provided, suitable for determining the presence of water in the lower part of the hollow body. The operation of the sensor will be illustrated in detail later on with reference to one of its possible embodiments.

Figure 2:
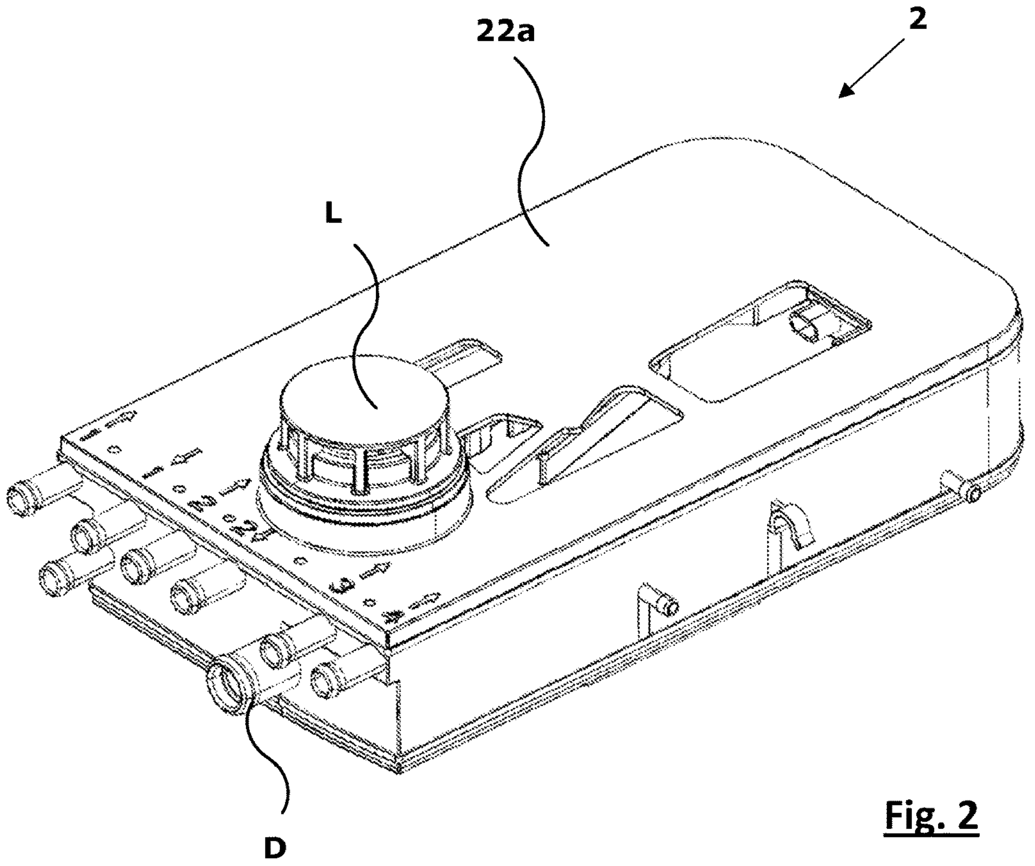
FIGS. 2 and 3 are perspective views of the front side and of the rear side of the device according to a preferred embodiment of the invention.
Figure 3:
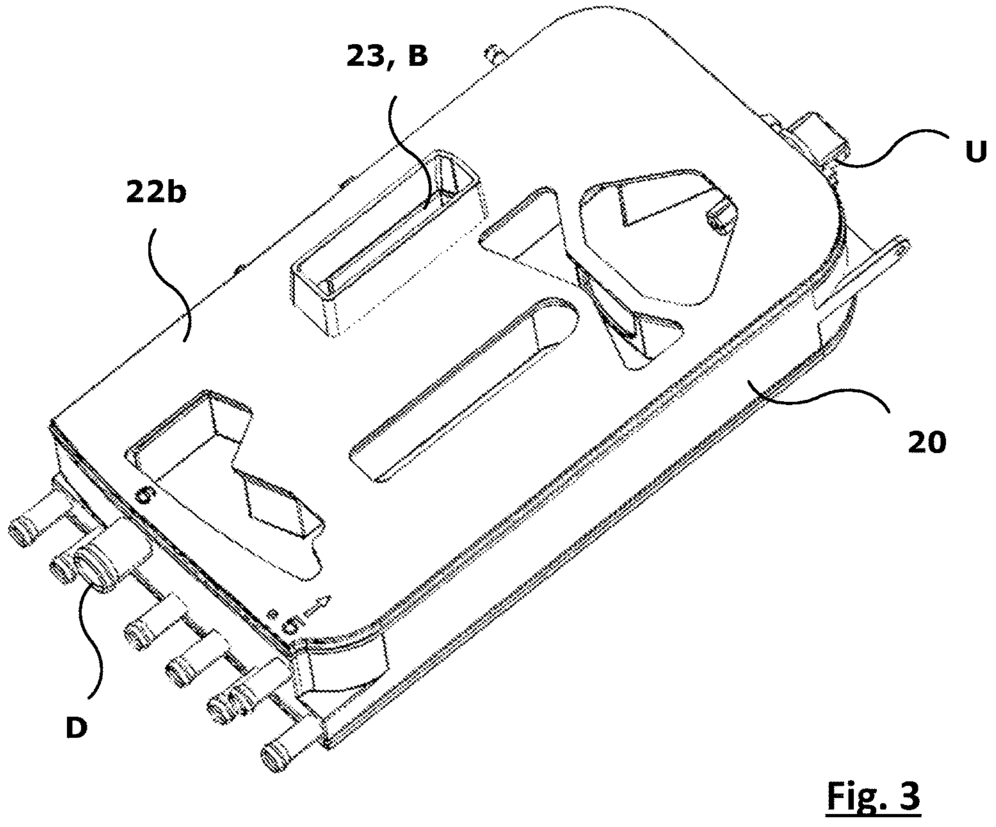
Figure 3A:
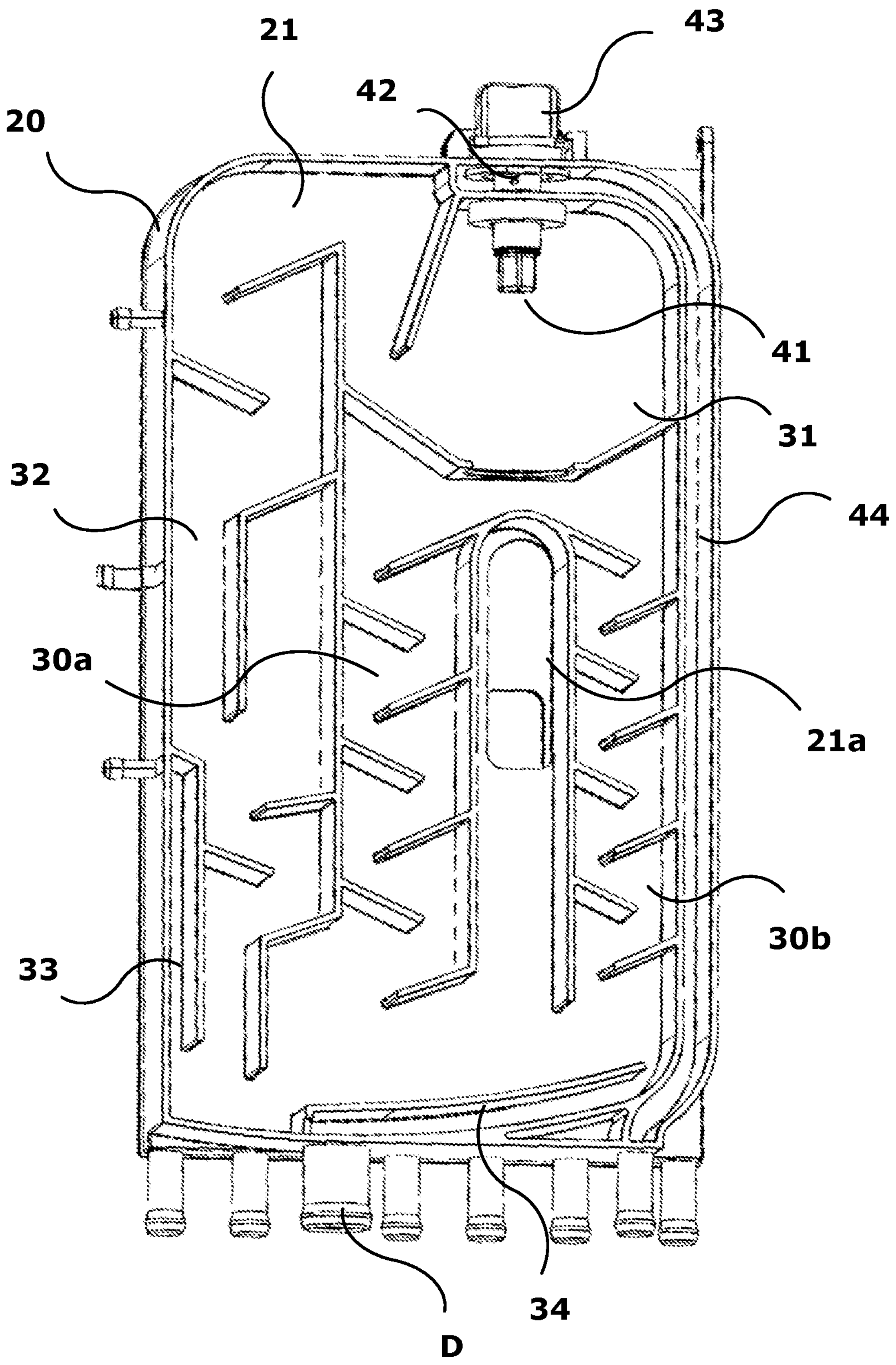

In FIGS. 2-3A, a preferred embodiment of the invention is illustrated.

In this case, the hollow condenser body is composed of a hollow box-shaped body 20, made for example of plastic material with possible details in steel, divided up longitudinally by a septum 21 into a feeding chamber (visible in FIG. 2A) and a condensation chamber (visible in FIG. 3A). The two opposed chambers divided by the septum 21 are closed to the outside by a front cover 22*a* and a rear cover 22*b* respectively, which in turn are equipped with openings for communication with other devices: in particular, the rear cover 22*b*, which closes the condensation chamber, is provided with an exhaust outlet 23 which forms the vent port B.

On the septum 21 an outflow port 21*a* is also made, placing the transit port L in fluid communication, via a guided path in the feeding chamber, with the condensation chamber.

Figure 2A:
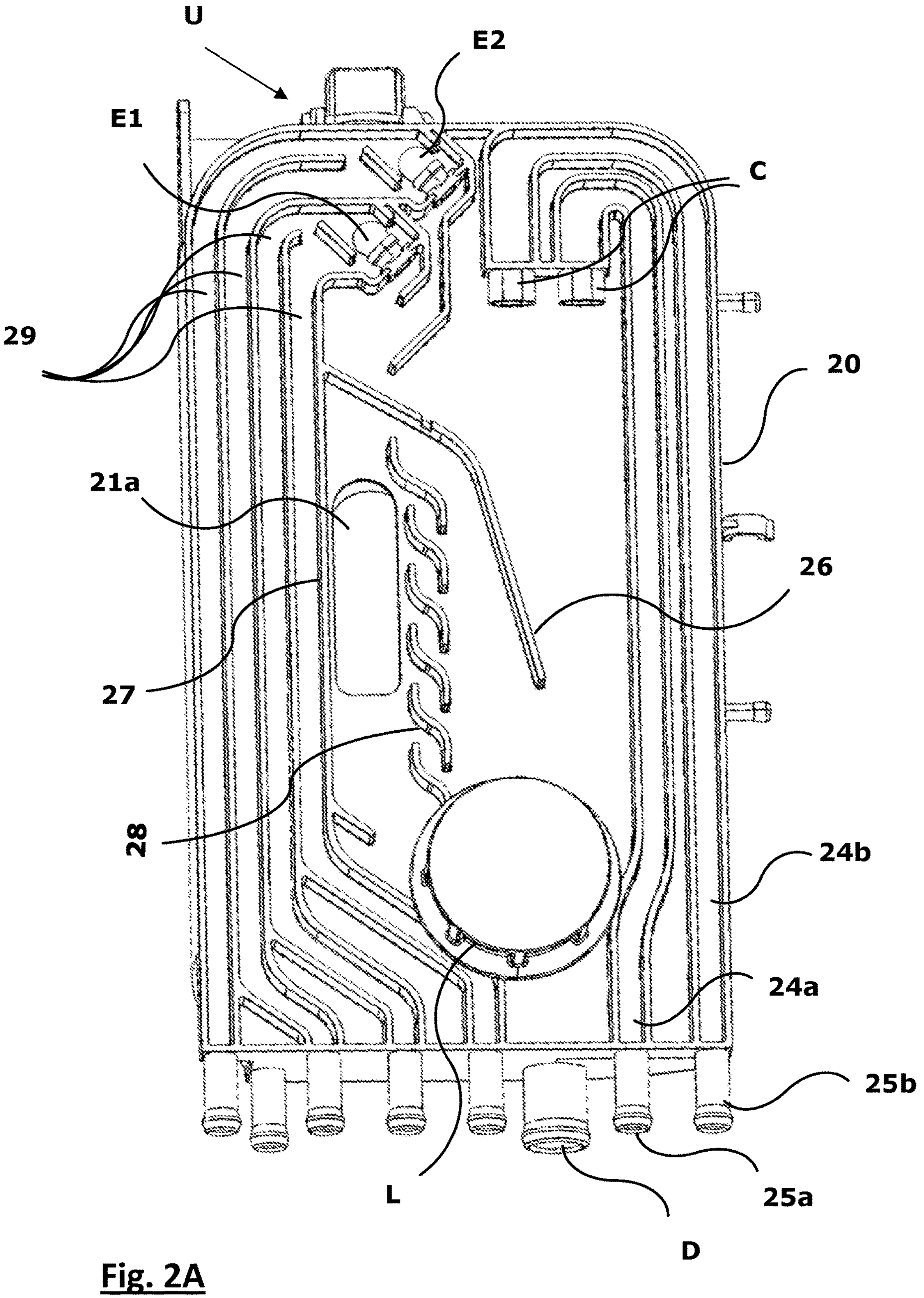
FIGS. 2A and 3A are views similar to those of FIGS. 2 and 3 respectively, with the covers removed.

Referring to FIG. 2A, it is noted that the feeding chamber has a plurality of ducts preferably made integrate with the septum 21 and then closed with the front cover 22*a*. In particular, feeding ducts 24*a* and 24*b*, which extend between respective hose connectors 25*a* and 25*b* arranged in the lower portion of the hollow box-shaped body 20, and corresponding feeding nozzles C arranged in the upper portion of the hollow box-shaped body 20, are provided. It is noted that the feeding nozzles C, intended to introduce water into the feeding chamber, terminate at a certain height (for example at least 10 mm and in a manner that is compatible with the applicable regulations) from the transit port L, so as to form an air gap which provides an anti-backflow function.

As represented, in the hollow box-shaped body 20, two separate feeding ducts 24*a* and 24*b* are preferably made, so as to supply to the feeding nozzles C two types of working fluid, for example on the one hand softened water and on the other hand demineralized water, even if this subdivision shall not be considered limiting.

In the feeding chamber there is preferably also provided a slanted rib structure 26 which has a dual function: on the one hand, it channels water from the feeding nozzles C to the transit port L for entry into the processing chamber 1 and, on the other hand, it channels the steam at the outlet from the processing chamber 1 towards the outflow port 21*a*. On the opposite side of the slanted rib structure 26, with respect to the outflow port 21*a*, there is provided another delimiting rib structure 27 and some deflectors 28 which slow down and channel the flow of steam.

According to a preferred embodiment, in the feeding chamber, there are provided additional transit ducts 29 for working fluids of a water softener (not represented in the drawings), equipped with respective hose connector which come out from the lower portion of the hollow box-shaped body 20, and respective vacuum break units E1 and E2.

In particular, the transit ducts 29 are represented by a pair of delivery and return ducts of a water softener, i.e. a softened water duct (which is hence connected externally to the device to one of the feeding ducts 24*a* or 24*b*) and a salt water (brine) duct for regenerating the water softener resins. Between the delivery and the return ducts 29, vacuum break units E1 and E2 are provided, which are used to draw air from the inside of the feeding chamber of the device. Thus, when a depression is generated in the ducts 29, air is freely drawn preventing, instead, a backflow of contaminated fluids to the water softener.

In FIG. 2A, the two vacuum break units E1 and E2 are represented schematically as ball valves, which remain closed when there is fluid pressure in the ducts 29 and open, allowing air to enter, when a depression arises in the ducts 29; it is understood that the vacuum break units E can even take on a different shape.

Referring now to FIG. 3A, it is noted that the condensation chamber has a plurality of deflectors, preferably made integrally with the septum 21, which define forced routes and traps for the steam which enters the condensation chamber via the outflow port 21*a*.

A labyrinth route is therefore produced in the condensation chamber for the steam which comes through from the port L, via the outflow port 21*a* and then is made to condense in order to be partly collected as condensate near a drain D and partly made to leave via the extraction exhaust outlet 23.

As represented, preferably on both sides of the outflow port 21*a*, two labyrinths 30*a* and 30*b* are provided, equipped with alternating inclined flat deflectors which define a confined pathway towards an upper converging chamber 31. In the latter, which is in the upper portion of the hollow box-shaped body 20, the condensation nozzle U is housed, designed in such a way as to spray atomized cold water downwards, so as to cross with the rising hot steam and produce the desired cooling and condensation. The upper converging chamber 31 then communicates with a pathway which rises upwards and then goes downwards to a disposal chamber 32 which is in communication with the extraction exhaust outlet 23.

As is well represented in FIG. 3A, the condensation nozzle U is preferably made up of a valve body having an end atomizing hole 41 and a lateral inlet hole 42. The valve body has a small external handgrip 43, by which it can be fitted and removed with a bayonet coupling on the hollow box-shaped condenser body 20. The liquid being supplied to the nozzle U is introduced via a duct 44 made in the hollow box-shaped body 20, which terminates close to the lateral inlet hole 42.

With this arrangement, the condensation nozzle U can easily be removed for maintenance and just as easily refitted to the device of the invention.

In the lower part of the disposal chamber 32 there is preferably arranged a water presence detection sensor T (not illustrated in FIG. 3A).

According to a preferred variant, the sensor T is a pressure sensor and is housed in a small measuring chamber 33 which is closed on its sides and open only on the bottom side. Thus, when the level of condensation water rises inside the hollow box-shaped body 20, it acts to close the measuring chamber 33 from the bottom and, rising further, compresses its internal volume, determining a corresponding detection of the pressure sensor. Thus, it is possible to precisely differentiate the level of water at the bottom of the hollow box-shaped body 20 of the device and detect the operational state.

Indeed, the condensation water, together with the sprayed water from the condensation nozzle U, precipitate downwards, to then be channeled by a collection chute 34 towards the drain D. Based on the flow rate of the drain D and on the production of steam condensation, the lower part of the hollow box-shaped body 20 is filled more or less with water, the level of which is detected by the sensor T.

The fact that the water presence detection sensor T is a pressure transducer must not be considered to be limiting, since a float or other means could also be used to detect water level. Even the position of the sensor T may be different from that illustrated.

The device according to the invention therefore incorporates the ducts and the associated anti-backflow units in a single condenser body, with higher manufacturing efficiency and reduction of space. Inside the same device, fluids of two separate cycles of the cleaning and disinfecting process are made to pass through. A first cycle provides for supplying water—preferably softened by a water softener inserted in the cleaning system—from the water supply network to the inside of the processing chamber 1. This phase of the cycle is achieved by enabling the device of the invention to intercept the ducts supplying water with anti-backflow, air break and vacuum break units. The water is fed into the chamber 1, making it come out from the nozzles C through an air gap which prevents any backflow. The water is directed by the inclined partition 26 towards the transit port L, from where it enters the chamber 1.

In the presence of a water softener, the system benefits from the device according to the invention since it offers the availability of ducts 29 equipped with respective vacuum break units E.

In the instance it is considered necessary to also use demineralized water, the second nozzle C is also used to feed it.

In the successive disinfecting and drying cycles, the steam produced in the chamber 1 comes out from the transit port L moving naturally from an area of higher pressure (hot cleaning chamber 1) to an area of low pressure (cold hollow condenser body), passing through the deflectors 28 and ending up in the condensation chamber via the outflow port 21*a*. In the condensation chamber, the steam is cooled upon contact with the cold walls and crossing the waterfronts which are formed in the two labyrinth routes 30*a* and 30*b* by means of sprayed water from the condensation nozzle U. The exhaust air, deriving from cooled and dehumidified steam, can therefore escape into the environment via the exhaust outlet 23 which is in communication with the disposal chamber 32. The condensate water and atomized water from the nozzle U precipitate into the lower part of the device and are discharged through the drain holes D.

As it is understood, the solution of the invention fully satisfies the objects disclosed in the preamble. The interception device of the invention, with a shape that is extremely compact and simple to manufacture, incorporates a plurality of ducts and anti-backflow, air break and vacuum break units, which allow to satisfy the regulatory requirements. In the event of malfunctions, the integrated device can easily be removed and replaced with a similar one, pending possible diagnostics and maintenance operations, without resulting in a prolonged stopping of the cleaning and disinfecting system.

It is understood that the invention must not be considered to be limited to the particular embodiment described and illustrated, but that different variants are possible, all within the reach of a skilled man in the art, without thereby departing from the scope of protection of the same invention, which is uniquely defined by the attached claims.

For example, the specific configuration of the hollow condenser body can vary, providing differently arranged septums and ducts for fluids. The preferred embodiment, equipped with only one longitudinal separation septum, is particularly efficient, but it is not the only one that can be devised. The separation between the fluid paths in the feeding chamber and in the condensation chamber can be achieved also by means of one or more septums of cylindrical or other shape.

It is even considered that the various fluid paths provided in the description of the preferred embodiment need not necessarily be present all together, but that only some of them may be provided. For example, it is conceivable to provide a simplified device in which the ducts 29 equipped with respective vacuum break units E are not incorporated.

Furthermore, the disposal chamber 32 could take a different shape to house a water presence detection sensor of a different nature.

Lastly, although in the description reference is always made to one transit duct A and to the associated transit port L, a plurality of them (for example two) can be provided. In particular, it is not ruled out that two separate ducts respectively for water feeding and for steam exhaust can be advantageously provided.

The invention claimed is:

1. A fluid interception device for a cleaning and disinfecting system for medical devices equipped with a processing chamber, the fluid interception device comprising:

a separation septum comprising at least one flow port; and a hollow box-shaped condenser body having an upper portion and a lower portion, the separation septum dividing the hollow box-shaped condenser body into a feeding chamber and a condensation chamber, the hollow box-shaped condenser body being provided with a transit port disposed at a side of the feeding chamber and configured to fluidly communicate with a cleaning and disinfecting system transit duct of said cleaning and disinfecting system, the transit port being in communication with said condensation chamber through the at least one flow port of the separation septum, a vent port in communication with an external environment of the fluid interception device, one or more condensation nozzles configured to spray water, the one or more condensation nozzles being configured to be in fluid communication with one or more drain holes disposed in said lower portion of said hollow box-shaped condenser body, and one or more water feeding nozzles disposed in said upper portion of said hollow box-shaped condenser body and above with respect to the transit port and configured to be in fluid communication with said transit port, wherein the separation septum is disposed between the one or more condensation nozzles and the one or more water feeding nozzles.

2. The fluid interception device as in claim 1, wherein said one or more water feeding nozzles are disposed at a distance from said transit port at a sufficient height to determine an air gap of at least 10 mm.

3. The fluid interception device as in claim 1, wherein said hollow box-shaped condenser body includes at least one softened water transit duct configured to be in communication with a water softener, each of the at least one softened water transit ducts being equipped with a respective vacuum break system.

4. The fluid interception device as in claim 1, wherein said hollow box-shaped condenser body includes a pair of water softener transit ducts configured to be in communication with a water softener, the pair of water softener transit ducts being equipped with respective vacuum break systems.

5. The fluid interception device as in claim 1, further comprising a water presence detection sensor configured to determine a level of water accumulated in the lower portion of said hollow box-shaped condenser body.

6. The fluid interception device as in claim 1, wherein said separation septum longitudinally divides said hollow box-shaped condenser body.

7. The fluid interception device as in claim 6, wherein said feeding chamber and the condensation chamber are opposite one another on either side of said separation septum and are closed to the outside by a front cover and a rear cover respectively, said rear cover being equipped with at least one exhaust outlet which forms said vent port.

8. The fluid interception device as in claim 1, wherein said feeding chamber and the condensation chamber have channeling paths configured to receive working fluids, the channeling paths being defined by ribs and deflectors integral with said separation septum.

9. A cleaning and disinfecting system for medical devices, the system comprising:

the fluid interception device as in claim 1;

a processing chamber; and one or more transit ducts for a transit of fluids, said one or more transit ducts configured to be in fluid communication with corresponding transit ports of the fluid interception device.

* * * * *